United States Patent
Palanganda Poonacha et al.

(10) Patent No.: US 9,869,634 B2
(45) Date of Patent: Jan. 16, 2018

(54) SYSTEM AND METHOD FOR DISSOLVED GAS ANALYSIS

(71) Applicant: General Electric Company, Schenectady, NY (US)

(72) Inventors: Samhitha Palanganda Poonacha, Karnataka (IN); Sandip Maity, Karnataka (IN); Nagapriya Kavoori Sethumadhavan, Karnataka (IN)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 224 days.

(21) Appl. No.: 14/837,052

(22) Filed: Aug. 27, 2015

(65) Prior Publication Data
US 2016/0061721 A1    Mar. 3, 2016

(30) Foreign Application Priority Data
Aug. 27, 2014  (IN) ............................ 4193/CHE/2014

(51) Int. Cl.
*G01N 21/25* (2006.01)
*G01N 21/39* (2006.01)
*G01J 3/433* (2006.01)
*G01N 21/3504* (2014.01)
(Continued)

(52) U.S. Cl.
CPC ............ *G01N 21/39* (2013.01); *G01J 3/4338* (2013.01); *G01N 21/031* (2013.01); *G01N 21/314* (2013.01); *G01N 21/3504* (2013.01); *G01N 2021/399* (2013.01); *G01N 2201/06113* (2013.01)

(58) Field of Classification Search
CPC .... G01N 21/39; G01N 21/031; G01N 21/314; G01N 21/3504; G01N 2021/399; G01N 2201/06113; G01J 3/4338

USPC ......................................................... 356/409
See application file for complete search history.

(56) References Cited

U.S. PATENT DOCUMENTS

| | | | |
|---|---|---|---|
| 7,683,357 B2 | 3/2010 | Von Drasek et al. | |
| 7,764,379 B1 | 7/2010 | McDermott | |
| 2008/0255769 A1 | 10/2008 | Zhou et al. | |
| 2009/0023222 A1* | 1/2009 | Wu ................. | A61B 5/14532 436/95 |
| 2011/0150035 A1 | 6/2011 | Hanson et al. | |
| 2011/0181879 A1 | 7/2011 | Chen et al. | |
| 2014/0036954 A1 | 2/2014 | Maity et al. | |
| 2014/0067282 A1 | 3/2014 | Beyer et al. | |

FOREIGN PATENT DOCUMENTS

| | | |
|---|---|---|
| CN | 102798610 A | 11/2012 |
| CN | 202974862 U | 6/2013 |

(Continued)

OTHER PUBLICATIONS

English translation of EP1873513.*

(Continued)

*Primary Examiner* — Hina F Ayub
(74) *Attorney, Agent, or Firm* — GE Global Patent Operation; Scott R. Stanley (57) ABSTRACT

A method implemented on a processor includes emitting a light beam from a light source to a component in an absorption cell, wherein the light beam comprises a plurality of wavelength beams. The method further includes generating a plurality of response signals due to the presence of the component, corresponding to the plurality of wavelength beams of the light beam. The method also includes detecting the plurality of response signals by a photo detector coupled to the absorption cell. The method includes determining a concentration of the component based on the plurality of response signals.

18 Claims, 7 Drawing Sheets

(51) Int. Cl.
*G01N 21/03* (2006.01)
*G01N 21/31* (2006.01)

(56) References Cited

FOREIGN PATENT DOCUMENTS

EP 1873513 A2 1/2008
JP 4038631 B2 1/2008

OTHER PUBLICATIONS

Serdyuchenko et al., "Application of Tunable Diode Laser Spectroscopy for Time Resolved Measurements in Electron-Beam Produced Plasma", Plasma Science, IEEE 34th International Conference on, pp. 307, Jun. 17-22, 2007.

McGettrick et al., "Tunable Diode Laser Spectroscopy With Wavelength Modulation: Calibration-Free Measurement of Gas Compositions at Elevated Temperatures and Varying Pressure", Journal of Lightwave Technology, IEEE, vol. No. 27, Issue No. 15, pp. 3150-3161, Aug. 1, 2009.

Cai et al., "Simultaneous measurement of CO and CO2 at elevated temperatures by diode laser wavelength modulated spectroscopy", Institute of Measurement and Control, May 23, 2012, pp. 2089-2095, vol. 45, Issue No. 8, London, GB.

Khan et al., "A compact, fast response synchronous measurement of temperature for UAV applications", SPIE, 2011, pp. 804606-1-11, vol. 8046.

Ning et al., "Calibration-free wavelength modulation spectrum of gas", Wuli Xuebao—Acta Physica Sinica, 2011, pp. 70701.1-70701.7, 2011, vol. 60, Issue No. 7.

European Search Report and Written Opinion issued in connection with corresponding EP Application No. 15182202.0 dated Jan. 25, 2016.

\* cited by examiner

SYSTEM AND METHOD FOR DISSOLVED GAS ANALYSIS

BACKGROUND

The subject matter disclosed herein relates to dissolved gas analysis using spectroscopy. Specifically, the subject matter relates to accurate measurement of gas concentrations using wavelength modulation spectroscopy.

Electrical equipment such as transformers use fluids such as castor oil, mineral oil and synthetic oils for insulation purposes. The parameters of the fluid are indicative of incipient faults in the electrical equipment. The parameters of the fluid among other things include information of total combustible gas (TCG). Examples of total combustible gas include carbon monoxide, carbon dioxide, hydrocarbons, oxygen and nitrogen. Specifically, carbon monoxide and carbon dioxide increase in concentration with thermal aging and degradation of insulation of the electrical equipment. Furthermore, hydrocarbons such as acetylene and ethylene increase in concentration due to dielectric breakdown caused due to corona and arcing. Further, concentrations of oxygen and nitrogen are indicative of condition of a gas pressurizing system of the equipment. Therefore, technique of dissolved gas analysis (DGA) is employed to determine the concentration of the gas components in the fluid used in the electrical equipment to predict the incipient fault.

Methods of analyzing the gas concentrations from the fluid samples extracted from the equipment employ spectroscopic techniques. Conventional spectroscopic techniques include off line DGA techniques and absorption spectroscopy based techniques. However, off line DGA techniques are affected by maintenance issues and uncertainties issues. Furthermore, techniques employing direct absorption spectroscopic signals are less sensitive with poor signal to noise ratio. In general, conventional spectroscopic techniques determine the concentrations of the gas component in a limited range of concentrations and are based on modulating the light beam to improve the sensitivity of detection. Measurements from spectroscopic techniques such as wavelength modulated spectroscopy are affected by the ambient conditions of the gas, especially the ambient pressure conditions of the dissolved gas.

For these and other reasons, newer techniques are needed to measure concentration of gas components over an extended range.

BRIEF DESCRIPTION

In accordance with one aspect of the present technique, a method is disclosed. The method includes emitting a light beam from a light source to a component in an absorption cell, wherein the light beam comprises a plurality of wavelength beams. The method further includes generating a plurality of response signals due to the presence of the component, corresponding to the plurality of wavelength beams of the light beam. The method also includes detecting the plurality of response signals by a photo detector coupled to the absorption cell. The method includes determining a concentration of the component based on the plurality of response signals.

In accordance with another aspect of the present technique, a system is disclosed. The system includes an absorption cell having a component and a light source emitting a light beam comprising a plurality of wavelength beams, to the component in the absorption cell to generate a plurality of response signals. The system also includes a photo detector coupled to the absorption cell for detecting the plurality of response signals corresponding to the plurality of wavelength beams of the light beam. The system further includes a processor communicatively coupled to the photo detector and configured to receive the plurality of response signals and determine a concentration of the component based on the plurality of response signals.

DRAWINGS

These and other features and aspects of embodiments of the present invention will become better understood when the following detailed description is read with reference to the accompanying drawings in which like characters represent like parts throughout the drawings, wherein.

DETAILED DESCRIPTION

Embodiments of systems and methods disclosed herein include emitting a light beam from a light source to a component in an absorption cell. The light beam comprises a plurality of wavelength beams. In response to the modulated light beam and due to the presence of the component, a plurality of response signals are generated in the absorption cell. The plurality of response signals correspond to the plurality of wavelength beams of the light beam. The plurality of response signals are detected by a photo detector coupled to the absorption cell. A concentration of the component is determined based on the plurality of response signals. In certain embodiments, the plurality of response signals include a first plurality of response signals generated by maintaining the component at a first ambient condition and a second plurality of response signals generated by maintaining the component at a second ambient condition. The concentration of the component is determined based on the first plurality of response signals and the second plurality of response signals.

The terms 'beam', 'radiation beam', 'light beam' and 'light beam', used herein equivalently and interchangeably, refers to the output of the light source 106. The term 'wavelength beam' refers to a beam of radiation having a specified wavelength. The term 'component' refers to a chemical element or a chemical compound in gaseous or liquid form dissolved or suspended in another liquid or a gas. The term 'absorption cell' used herein refers to a chamber or a container wherein the component interacts with the light beam to generate spectroscopic signals. The term 'response signal' referred herein includes, but not limited to, spectroscopic signals generated during interaction of the modulated light beam with the component. The term 'concentration' refers to the strength of the component in a fluid or the number of molecules per unit volume. The term 'stored response' referred herein includes, but not limited to, a pre-calibrated spectroscopic response of a component at a plurality of concentrations interacting with a light beam having a plurality of wavelength beams. The stored response is determined apriori and is available for retrieval from a memory storage. The term reference value is any one or a combination of a plurality of response values, a concentration strength and a slope value selected from the stored response.

Figure 1:
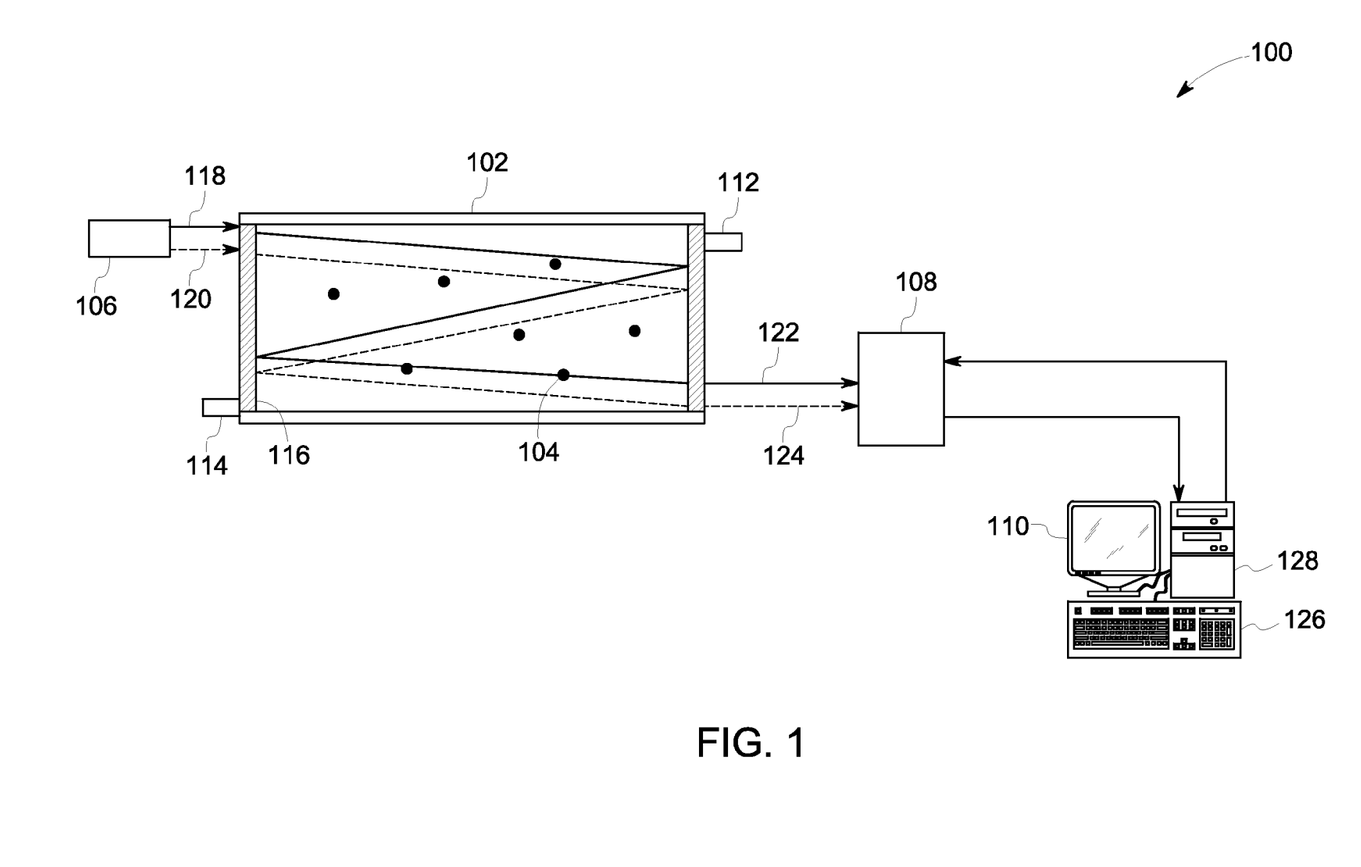
FIG. 1 is a diagrammatic illustration of a system for determining a concentration of a component in accordance with an exemplary embodiment.

FIG. 1 is a system 100 for determining a concentration of a component in accordance with an exemplary embodiment. The system 100 includes an absorption cell 102 having a component 104. The system 100 includes a light source 106, a photo detector 108 and a computer system 110. In an exemplary embodiment, the system 100 is a spectroscopic system. The light source 106 generates electromagnetic radiations in the form of light beams having multiple wavelengths.

The absorption cell 102 is a chamber of suitable dimension with an inlet 112 and an outlet 114 for introducing the component into the chamber and extracting the component out of the chamber respectively. In one embodiment, the length of the absorption cell is about one meter. The cell 102 is a multi-pass absorption cell having reflective surfaces 116 for increasing the path length of the light beam. In alternative embodiment, the cell 102 may be a single pass absorption cell. The absorption cell 102 may have a provision to maintain or measure ambient conditions of the component 104. The ambient conditions include, but are not limited to, a temperature setting, a pressure setting and combinations thereof. In one embodiment, additional control mechanisms (not shown in FIG. 1) may be provided with the inlet 112 and outlet 114 for controlling the ambient pressure of the component by varying the pressure inside the absorption cell. In another embodiment, the temperature of the absorption cell may be changed and thereby the ambient temperature of the component may be controlled. In some embodiments, the absorption cell may contain the component dissolved or suspended in a liquid, a gas or a solid material. As an example, in one embodiment, the absorption cell contains a fluid having the component dissolved in a liquid. The component may include acetylene, hydrogen, methane, ethane, ethylene, $CO_2$ and the combinations thereof.

In one embodiment, the light source 106 may be a laser light source generating a modulated light beam. In an exemplary embodiment, the light beam is a wavelength modulated laser beam emitted from a modulated light source. In some embodiments, the light beam is wavelength scanned and modulated. In some embodiments, the light source 106 is a tunable diode (TD) laser source, or a quantum cascade laser source. Alternatively, the light source 106 may generate a frequency modulated light beam. In the embodiment where the light source 106 is wavelength modulated, the light beam includes a plurality of wavelength beams 118, 120. In one embodiment, the plurality of wavelength beams 118, 120 are multiplexed in sequential time slots. Although the plurality of wavelength beams 118, 120 are illustrated in the light beam, only one of the wavelength beams is transmitted through the absorption cell 102. Each of the plurality of wavelengths 118, 120 interacts with the component 104 during transmission through the absorption cell 102. The interaction of the plurality of wavelength beams with the component in the absorption cell generates a plurality of response signals 122, 124. The response signal 122 corresponds to the wavelength beam of 118 and the response signal 124 corresponds to the wavelength beam 120. In embodiments disclosed herein, the plurality of response signals 122, 124 are spectroscopic response signals. It should be noted that the type of response signals is not limited to be generated by spectroscopic techniques, and the number of the plurality of response signals is not limited to two signals 122, 124.

In some embodiments, the plurality of response signals are generated due to absorption of the radiation energy of the beam by the component. The plurality of response signals generated from a direct absorption spectroscopic technique is referred herein as 'direct absorbance signal'. In other embodiments, the modulated light beam generates a plurality of response signals (via the component) corresponding to a plurality of harmonics of the modulation frequency. One or more of the plurality of response signals corresponding to the plurality of harmonics may be considered for further processing as explained in subsequent paragraphs.

In one exemplary embodiment, a first plurality of response signals are generated when the component is maintained at a first ambient condition. A second plurality of response signals are generated when the component is maintained at a second ambient condition. The first plurality of response signals and the second plurality of response signals include spectroscopic signals generated due to interaction of the component with the first wavelength beam and the second wavelength beam. The concentration of the component is determined based on the first plurality of response signals and the second plurality of response signals. The working of this embodiment does not require information about the ambient conditions and thus the measurement of concentration of the component is not affected by the presence of errors in ambient pressure measurement or ambient temperature measurements. The details of the technique of measuring the concentration of the component based on the first plurality of response signals and the second plurality of response signals are disclosed herein with reference to subsequent figures.

The photo detector 108, coupled to the absorption cell, detects the plurality of response signals 122, 124 and provides them to the computer system 110. In one embodiment, detecting the plurality of response signals includes measuring a direct absorbance signal. In another embodiment, photo detector 108 detects a first amplitude of a first response signal and a second amplitude of a second response signal, wherein the first response signal and the second response signal correspond to two distinct harmonics of modulating frequency of the wavelength modulated laser beam. In another embodiment, the photo detector 108 detects response signals due to two consecutive harmonic signals. In one embodiment, the photo detector 108 detects the first response corresponding to the first ambient condition and the second response corresponds to the second ambient condition. In one embodiment, the computer system 110 includes a processor 126 communicatively coupled to the photo detector and configured to receive the plurality of response signals. The processor 126 may further process the plurality of response signals. In one embodiment, where the first harmonic response and the second harmonic response signals are received, the second harmonic response signal is normalized by the first harmonic response signal. Specifically, the first amplitude of the first response signal is normalized by the second amplitude of the second response signal. In another embodiment where two response signals corresponding to successive harmonic signals are received, the response corresponding to one harmonic signal is normalized by the response corresponding to another harmonic signal. The computer system 110 also includes a memory 128 for storing program, and the plurality of detected response signals 122, 124. The processor 126 is also configured to determine a concentration of the component based on the plurality of response signals 122, 124. In some embodiments, the computer system 110 may also include a plurality of input devices such as keyboard, mouse and a plurality of output devices such a monitor, and speaker.

The processor 126 includes at least one arithmetic logic unit, a microprocessor, a general purpose controller or a processor array to perform the desired computations or run the computer program. In one embodiment, the functionality of the processor 126 may be limited to controlling the operation of the light source 106. In another embodiment, the functionality of the processor 126 may be limited to controlling the operation of the photo detector 108. In another embodiment, the functionality of the processor 126 is limited to determining the concentration of the component present in the absorption cell. In some exemplary embodiments, functionality of at least one processor module would include assisting the operation of one or more of the light source, and photo detector. While the processor 126 is shown as a single unit, there can be more than one processor module embedded in the light source and the photo detector cooperatively operating to detect the concentration of the component.

The memory 128 may be a non-transitory storage medium. For example, the memory 128 may be a dynamic random access memory (DRAM) device, a static random access memory (SRAM) device, flash memory or other memory devices. In one embodiment, the memory 128 may include a non-volatile memory or similar permanent storage device, media such as a hard disk drive, a floppy disk drive, a compact disc read only memory (CD-ROM) device, a digital versatile disc read only memory (DVD-ROM) device, a digital versatile disc random access memory (DVD-RAM) device, a digital versatile disc rewritable (DVD-RW) device, a flash memory device, or other non-volatile storage devices. In one specific embodiment, a non-transitory computer readable medium may be encoded with a program to instruct the processor 126 to determine the concentration of the component.

In some embodiments, the memory 128 stores the stored response in the form of tables. Exemplary embodiments of determining the concentrations of the component using the stored response are explained herein. In some embodiments, the stored response includes a plurality of entries in a table with each entry having a plurality of wavelength values of the light beam, a plurality of spectroscopic response signals corresponding to the wavelength values, a slope value of a characteristic line joining a plurality of spectroscopic response signals corresponding to a plurality of ambient conditions and a corresponding concentration value. In few other embodiments, the stored response may be stored in the form of two tables, a first table providing a slope value and a second table providing the concentration value. The stored response corresponds to a reference ambient condition. The stored response may be represented as a graph and is referred here in as 'reference response'. The plurality of entries of the stored response corresponds to points on the reference response and are referred herein as reference response values. The processor 126 is configured to determine a reference response value from the plurality entries of the stored response. In an alternate embodiment, the processor 126 is configured to project plurality of response signals on to a reference response to determine a reference response value.

Figure 2:
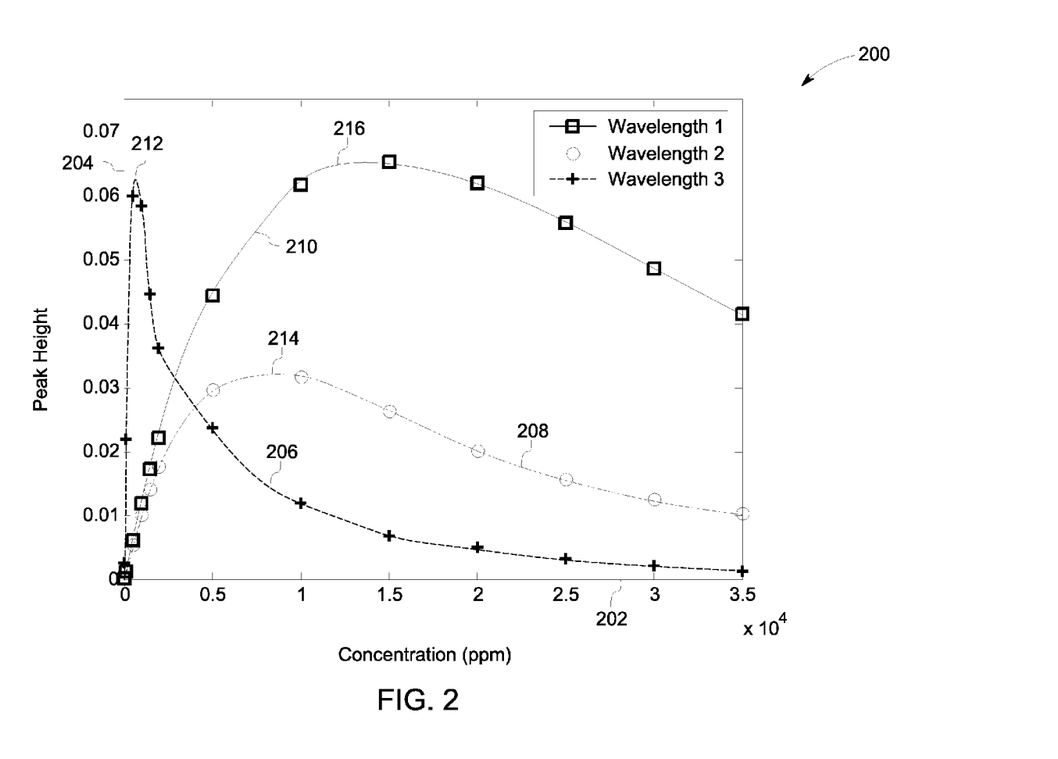
FIG. 2 is a graph illustrating a plurality of reference response signals corresponding to a plurality of wavelengths for different concentrations of the component in accordance with an exemplary embodiment.

FIG. 2 is a graph 200 illustrating a plurality of reference response curves corresponding to a plurality of wavelength beams for different concentrations of a component in accordance with an exemplary embodiment. The graph 200 includes an x-axis 202 representative of concentration in parts per million (ppm) units. The graph 200 also includes a y-axis 204 representative of response signal corresponding to second harmonic of the modulation frequency of the wavelength beam. The graph 200 illustrates curves 206, 208, 210 representative of response of acetylene (C2H2) interacting with the light beams having wavelengths 3021.65 nm, 3021.5 nm and 3021 nm respectively.

The curve 206 corresponding to the wavelength 3021.65 nm exhibits increasing trend when the concentration of the component is below 400 ppm. Above 400 ppm, the curve 206 exhibits a decreasing trend. For a range of concentrations with concentrations both above and below 400 ppm, the response signal values and the corresponding concentration values are not uniquely defined. As an example, a response signal value would be 0.03 for two concentration values of 200 ppm and 3500 ppm. Therefore, the wavelength beam 3021.65 nm may be used to detect concentrations only up to 400 ppm. Similarly, the wavelength beam 3021.5 nm (response curve 208) is used to detect concentration of acetylene up to 10000 ppm. As another example, the wavelength beam 3021 nm (response curve 210) is capable of detecting acetylene concentrations up to 15000 ppm. The detection limits for the curves 206, 208, 210 are represented by corresponding peak points 212, 214, 216 in the illustration. The curves 206, 208, 210 exhibit decreasing trend beyond the points 212, 214, 216 respectively. The embodiments related to subsequent figures, disclose techniques for measuring the concentration of the component over an extended range. As an example, the response signals corresponding to wavelength beams 3021.5 nm and 3021 nm may be used to measure the concentration of the component up to a range of 35000 ppm.

Figure 3:
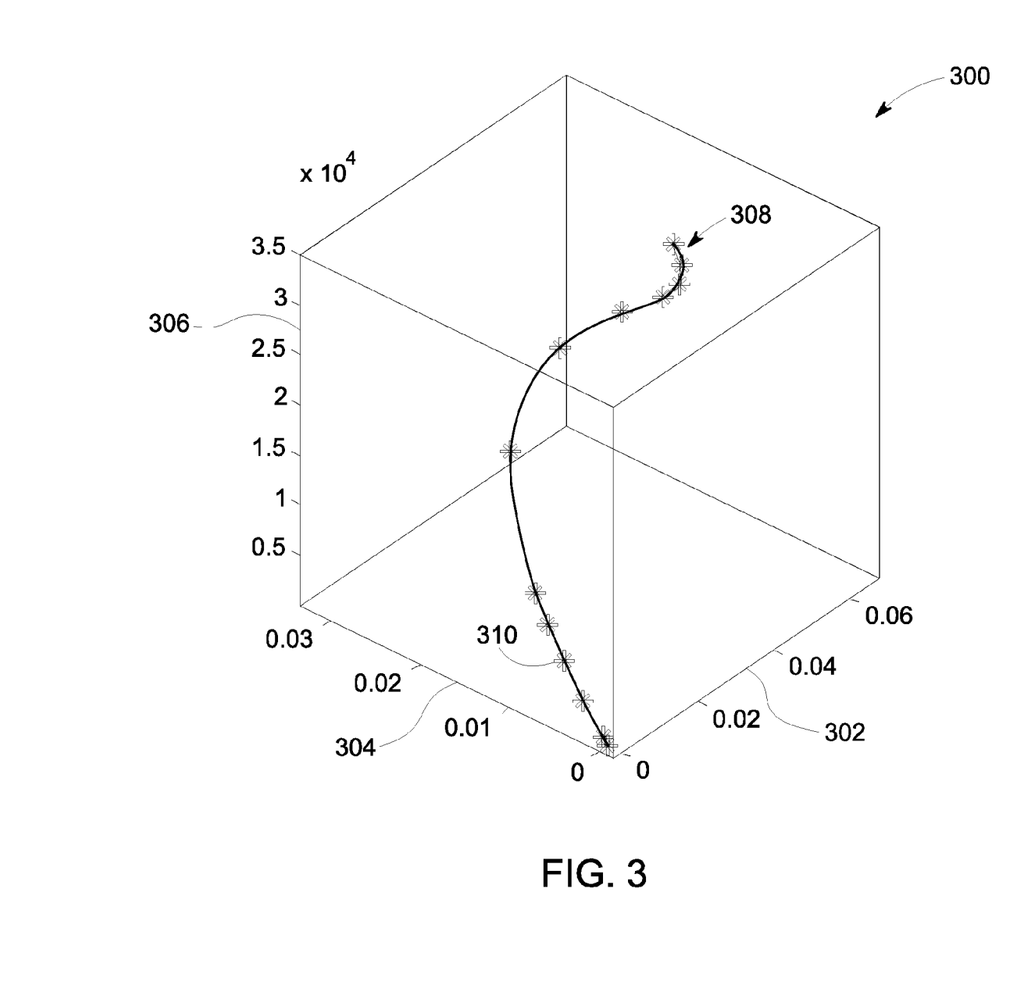
FIG. 3 is a graph in three dimensional co-ordinate system illustrating concentration of the component as a function of a plurality of response signals in accordance with an exemplary embodiment.

FIG. 3 is a graph 300 illustrating concentration of the component for a plurality of response signals in accordance with an exemplary embodiment. The graph 300 is a 3-D graph of the concentration of the component as a function of a first response and the second response signals corresponding to two beams of wavelengths of 3021.5 nm and 3021 nm. The x-axis 302 of the graph 300 is representative of first response corresponding to a first wavelength beam and the y-axis 304 is representative of second response corresponding to the second wavelength beam. The z-axis 306 is representative of concentration in parts per million (ppm) of the component. The curve 308 is three dimensional and is non intersecting over a concentration range of 0 ppm to 35000 ppm. As an example, a point 310 on the curve 308 corresponds to a concentration of 5000 ppm and has a first response peak magnitude of 0.01 on the x-axis 302 and a second response peak magnitude of 0.1 on the y-axis 304.

Figure 4:
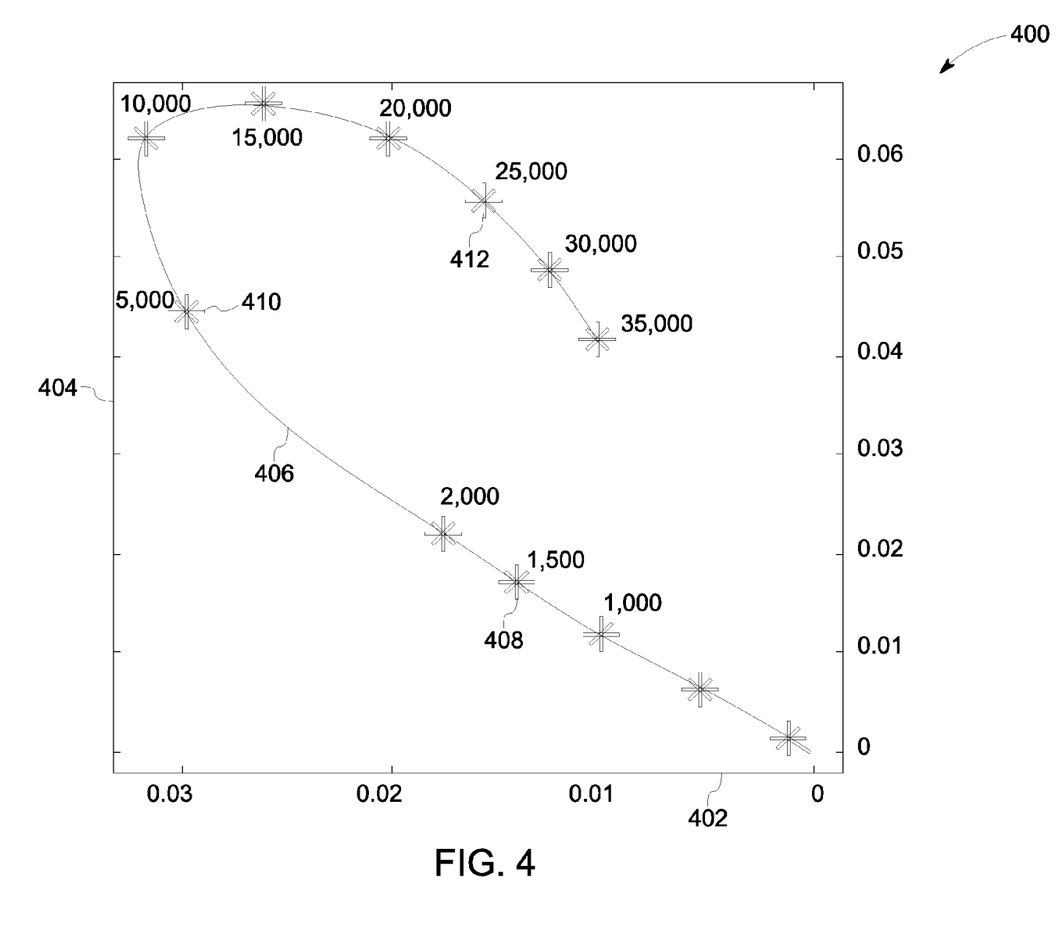
FIG. 4 is a graph in two dimensional co-ordinate system of FIG. 3 illustrating unique combinations of the plurality of response signals in accordance with an exemplary embodiment.

FIG. 4 is a graph 400 illustrating top view of FIG. 3 illustrating unique combinations of the plurality of response signals in accordance with an exemplary embodiment. The x-axis 402 is representative of first response corresponding to the first wavelength beam and the y-axis 404 is representative of the second response corresponding to the second wavelength beam. The curve 406 is two dimensional response illustrating a top view of the 3-D curve 308 of FIG. 3. The curve 406 is non-intersecting and each point on the curve corresponds to a unique combination of the first response value and the second response value. A plurality of points 408, 410, 412 are marked on the curve 406 for illustration purposes. The point 408 corresponds to 1500 ppm concentration of the component, the point 410 corresponds to 5000 ppm concentration of the component and the point 412 corresponds to 25000 ppm concentration of the component.

Figure 5:
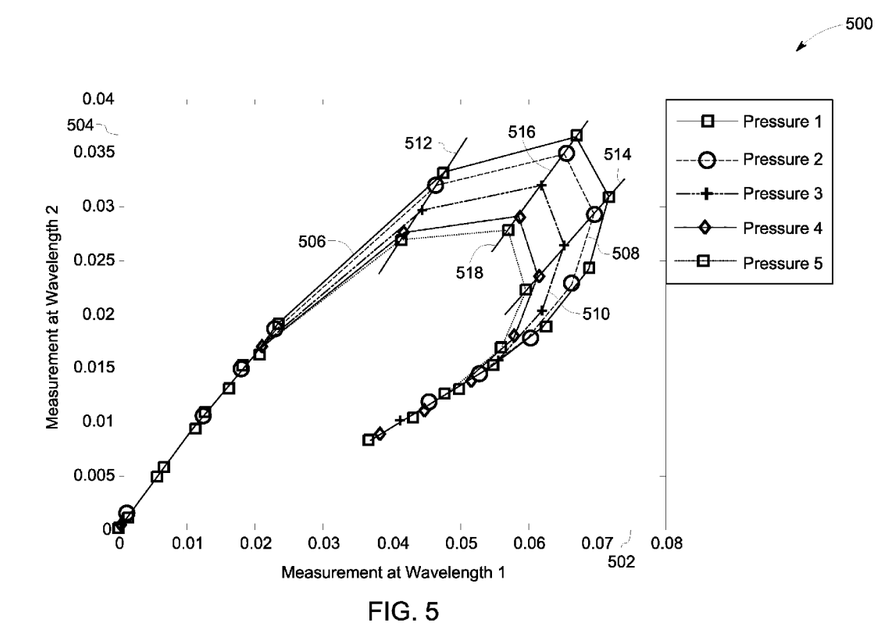
FIG. 5 is a graph illustrating a plurality of curves representing concentration as a function of plurality of response signals corresponding to a plurality of ambient conditions in accordance with an exemplary embodiment.

FIG. 5 is a graph 500 illustrating a plurality of two dimensional response signals corresponding to a plurality of ambient conditions in accordance with an exemplary embodiment. The x-axis 502 of the graph 500 is representative of a first response and the y-axis 504 is representative of a second response. The graph 500 includes six two dimensional response signals corresponding to six distinct ambient conditions of the component. For illustration purposes, three curves 506, 508, 510 among the plurality of curves are considered. In the illustration, the curves 506, 508, 510 correspond to a plurality of response signals from the component maintained at an ambient pressure of 235 Torr, 250 Torr and 265 Torr respectively. A plurality of lines 512, 514, 516 illustrated in the graph 500 are characteristic lines corresponding to a plurality of concentration values. The plurality of lines 512, 514, 516 includes points on the plurality of curves 506, 508, 510 corresponding to the same concentration of the component. Each of the plurality of lines 512, 514, 516 has a corresponding slope value. The slope value indicates a characteristic parameter of the concentration of the component.

An exemplary embodiment of determining the concentration of the component based on the first plurality of response signals and the second plurality of response signals is explained herein. The graph 500 includes a first point 518 representative of the first plurality of response signal corresponding to the first ambient pressure value i.e., 265 Torr. The graph also includes a second point 520 representative of the second plurality of response signal corresponding to the second ambient pressure value i.e., 235 Torr. The first point 518 and the second point 520 are representative of the same concentration of the component maintained at two different ambient pressure values. The line 516 joining the first point 518 and the second point 520 includes other points representative of the same concentration of the component maintained at other ambient pressure values. The slope value of line 516 is characteristic of the concentration of the component. The concentration of the component is determined based on the slope value of the line 516.

In one embodiment, combinations of the first response corresponding to the first wavelength beam and the second response corresponding to the second wavelength beam at a plurality of ambient conditions is stored in the memory. For each of the combination involving the first response and the second response, a concentration value is also stored. The first response and the second response are used to retrieve the concentration of the component from the memory. In one embodiment, an equation of a characteristic line joining the first response and the second response is determined. A reference response value is determined as a point of intersection of the characteristic line with the reference response. The concentration of the component is determined based on the reference response value. In another embodiment, a slope value associated with each of the combination of the first response and the second response are stored in the memory. In embodiments, where, a slope of the characteristic line representative of the ambient pressure variations is available, the concentration of the component is determined based on the slope value.

Figure 6:
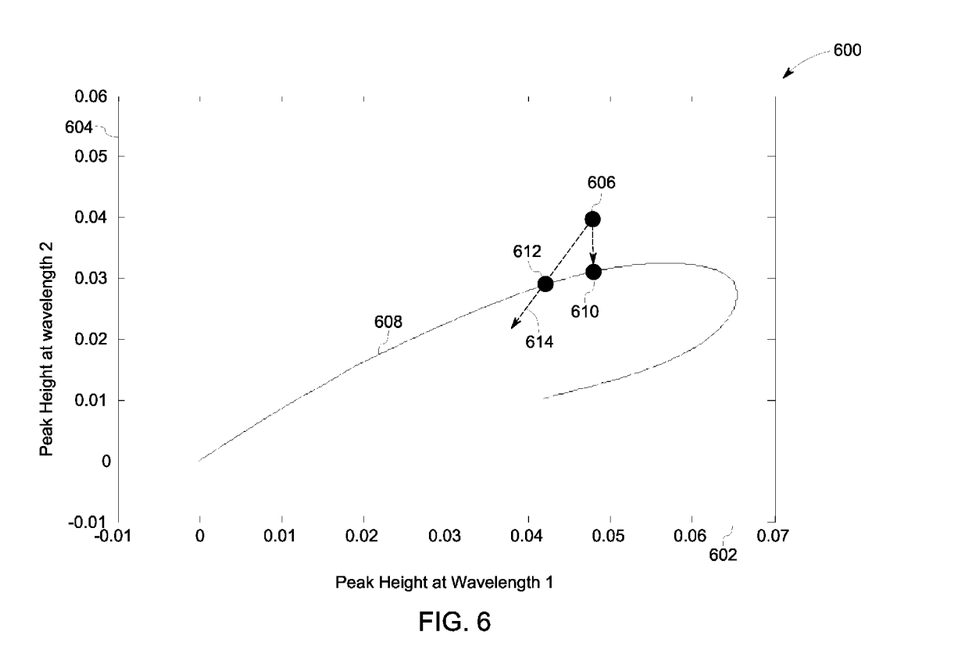
FIG. 6 is a graph illustrating non-orthogonal projection technique for determining concentration of a component using the system of FIG. 1.

FIG. 6 is a graph 600 illustrating a technique of determining the concentration of the component by projecting a measurement onto a reference response in accordance with an exemplary embodiment. The graph 600 has an x-axis 602 representative of the first response corresponding to the first wavelength beam and a y-axis 604 representative of the second response corresponding to the second wavelength beam. A point 606 is representative of a plurality of response signals comprising specific values of the first response and the second response. The graph 600 illustrates a curve 608 representative of a reference response corresponding to a reference ambient condition for a plurality of concentrations. Each point on the reference response 608 is associated with a specific concentration. The reference response 608 includes a true reference point representative of the concentration of the component.

The point 606 is projected on the curve 608 and the concentration value corresponding to the projected point on the curve 608 is determined as the concentration of the component. The projection of the point 606 on the curve 608 refers to the projection of the plurality of response signals on to the reference response. The projection operation is performed by determining a nearest point 610 on the curve 608 to the point 606. The nearest point can be determined using any of the standard methods available. In one embodiment, the nearest point 610 is determined using an orthogonal projection technique. A concentration value corresponding to the nearest point 610 is determined as the concentration of the component.

It should be noted herein that in certain cases, the orthogonal projection value for determining the nearest point 610 may not be an optimal projection of the measured point 606 on to the reference response 608 and could give rise to large errors in the determined concentration. In such cases, a non-orthogonal projection technique explained herein can determine a better estimate 612 of the true reference point. A slope value of a characteristic line representative of the concentration value is retrieved from the memory based on the nearest point 610. A projection line 614 is determined based on the measurement point 606 and the retrieved slope value. The point of intersection of the line 614 with the reference response 608 is determined as the better estimate 612. The concentration of the component corresponding to the point 612 is determined In an alternate embodiment, a slope value corresponding to the point 612 is retrieved from the memory. In one exemplary embodiment, the projection line 614 is determined based on additional parameters associated with the nearest point 610. In such an embodiment, the projection line 614 is not a straight line. As an example, a quadratic curve having the nearest point 610 may intersect the reference response 608 to determine the better estimate 612.

Figure 7:
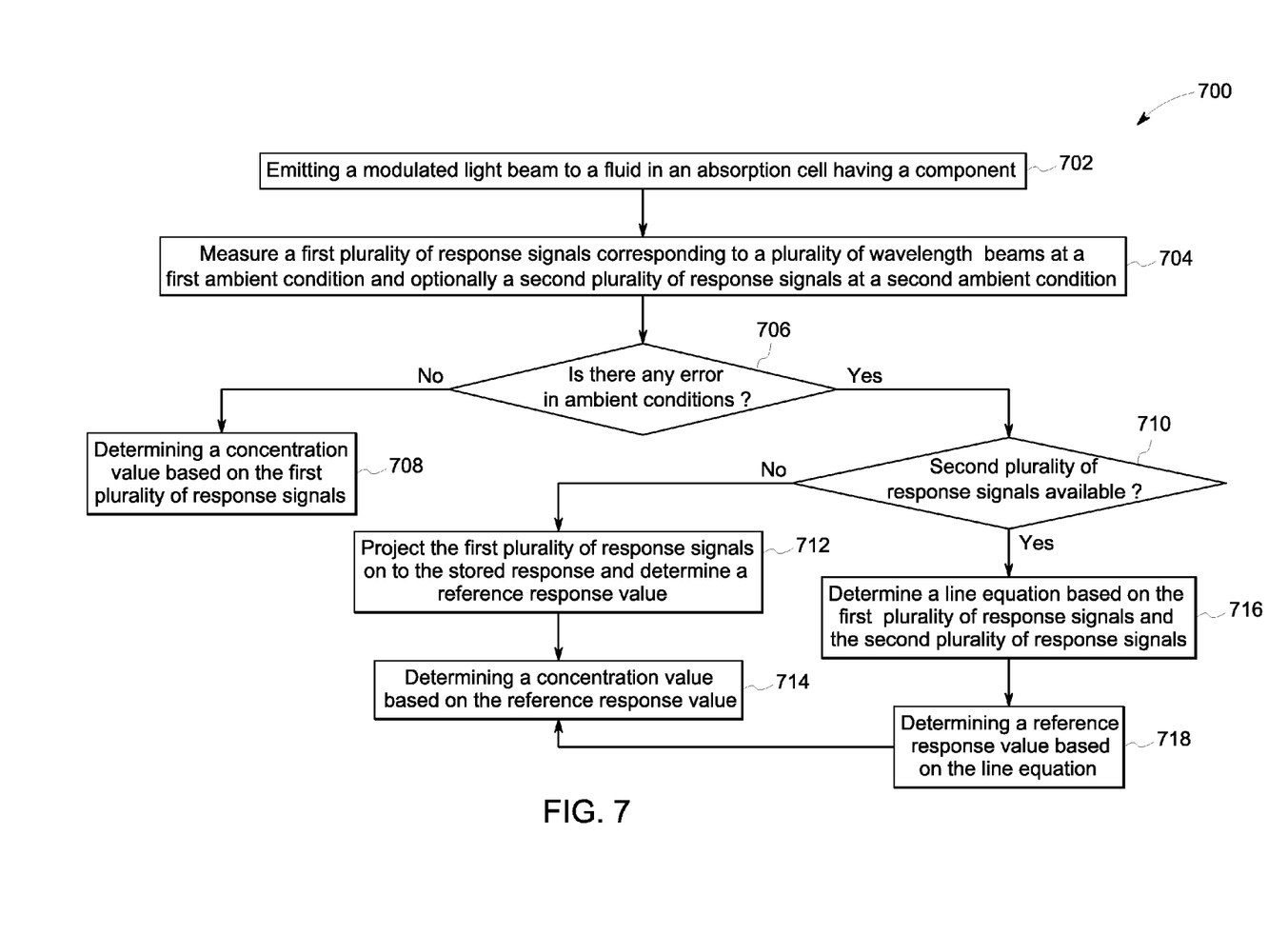
FIG. 7 is a flow chart of a method for determining concentration of a component in accordance with an exemplary embodiment.

FIG. 7 is a flow chart 700 of a method for determining concentration of a component in accordance with an exemplary embodiment. In step 702, the method includes emitting a modulated light beam from a light source to a component in an absorption cell, wherein the modulated light beam comprises a plurality of wavelength beams. The modulated light beam transmitting in the absorption cell interacts with the component to generate spectroscopic signals. In step 704, a plurality of response signals, representative of spectroscopic signals, are generated due to the presence of the component, corresponding to the plurality of wavelength beams of the modulated light beam.

In some embodiments, there may be variations in ambient conditions of the component. In such conditions, a modified technique of determining the concentration of the component is disclosed. The ambient condition of the component is also referred herein as 'first ambient condition' and the plurality of response signals corresponding to the first ambient condition is also referred herein as 'first plurality of response signals'. Variations in ambient pressure or temperature of the component modify the first plurality of signals. In step 706, a conditional test is performed to determine the presence of variations (or errors) in the ambient conditions. If there is no error in the ambient pressure or temperature value, the concentration of the component is determined in step 708 based on the first plurality of response signals.

In the case of variations in the ambient pressure values, the measurement of the first plurality of signals may differ from a reference response. In step 710, a conditional test is performed to determine the availability of a second plurality of response signals at a second ambient condition. If the second plurality of response signals are not available, the first plurality of response signals are projected on to the reference response. In step 712, a non-orthogonal projection technique is used to determine a reference response value. In step 714, the concentration of the component is determined based on the reference response value.

In an exemplary embodiment, a second plurality of response signals may be measured at a second ambient condition in step 704. In embodiments, where the second plurality of response signals are available, a line equation for a characteristic line is determined based on the first plurality of response signals and the second plurality of response signals as in step 716. A reference response value is determined in step 718 based on the line equation. In this embodiment, the reference response value is a point of intersection of the line equation with the reference response. A concentration of the component is determined based on the reference response value as explained previously using step 714. In one embodiment, a slope value of the line equation is determined and the concentration of the component is determined based on the slope value.

It is to be understood that not necessarily all such objects or advantages described above may be achieved in accordance with any particular embodiment. Thus, for example, those skilled in the art will recognize that the systems and techniques described herein may be embodied or carried out in a manner that achieves or improves one advantage or group of advantages as taught herein without necessarily achieving other objects or advantages as may be taught or suggested herein.

While the technology has been described in detail in connection with only a limited number of embodiments, it should be readily understood that the specification is not limited to such disclosed embodiments. Rather, the technology can be modified to incorporate any number of variations, alterations, substitutions or equivalent arrangements not heretofore described, but which are commensurate with the spirit and scope of the claims. Additionally, while various embodiments of the technology have been described, it is to be understood that aspects of the specification may include only some of the described embodiments. Accordingly, the specification is not to be seen as limited by the foregoing description, but is only limited by the scope of the appended claims.

The invention claimed is:

1. A method, comprising:
emitting a light beam from a light source to a component in an absorption cell, wherein the light beam comprises a plurality of wavelength beams;
generating a first plurality of response signals in the absorption cell corresponding to the plurality of wavelength beams of the light beam when the component is maintained at a first ambient condition;
generating a second plurality of response signals in the absorption cell corresponding to the plurality of wavelength beams when the component is maintained at a second ambient condition, the second ambient condition being different than the first ambient condition;
detecting the first plurality of response signals and the second plurality of response signals from the absorption cell by a photo detector coupled to the absorption cell; and
determining a concentration of the component based on the first and second plurality of response signals by:
processing the detected first and second plurality of response signals to generate a graph, an x-axis of the graph being representative of the first plurality of response signals and a y-axis of the graph being representative of the second plurality of response signals, the graph comprising a plurality of curves corresponding to unique combinations of values of the first and second plurality of response signals;
determining a first point on the graph representative of a first predetermined concentration of the component at the first ambient condition and a second point on the graph representative of a second predetermined concentration of the component at the second ambient condition, wherein a slope of a line joining the first and second points is representative of the concentration of the component; and
determining the concentration of the component based on the slope.

2. The method of claim 1, wherein each of the first ambient condition and the second ambient condition comprises at least one of a temperature setting and a pressure setting.

3. The method of claim 1, wherein emitting the light beam comprises emitting a wavelength modulated laser beam from a modulated light source.

4. The method of claim 3, wherein detecting the first plurality of response signals and the second plurality of response signals comprises measuring a first amplitude of a first response signal and a second amplitude of a second response signal, wherein the first response signal and the second response signal correspond to two distinct harmonics of modulating frequency of the wavelength modulated laser beam.

5. The method of claim 4, further comprises normalizing the first amplitude by the second amplitude.

6. The method of claim 1, wherein detecting the first plurality of response signals and the second plurality of response signals comprises measuring a direct absorbance signal.

7. The method of claim 1, wherein determining the concentration of the component comprises projecting the first and second plurality of response signals on to a reference response to determine a reference response value.

8. The method of claim 7, wherein determining the concentration of the component comprises projecting the first and second plurality of response signals on to the reference response using a non-orthogonal projection technique.

9. The method of claim 1, wherein the component comprises acetylene, hydrogen, methane, ethane, ethylene, carbon dioxide, moisture, carbon monoxide, or combinations thereof.

10. A system, comprising:

an absorption cell having a component;

a light source emitting a light beam comprising a plurality of wavelength beams, to the component in the absorption cell to generate a first plurality of response signals in the absorption cell when the component is maintained in a first ambient condition and to generate a second plurality of response signals in the absorption cell when the component is maintained in a second ambient condition the first ambient condition and the second ambient condition being different;

a photo detector coupled to the absorption cell, for detecting the first and second plurality of response signals corresponding to the plurality of wavelength beams of the light beam; and a processor communicatively coupled to the photo detector and configured to:

receive the first and second plurality of response signals;

process the detected first and second plurality of response signals to generate a graph, an x-axis of the graph being representative of the first plurality of response signals and a y-axis of the graph being representative of the second plurality of response signals, the graph comprising a plurality of curves corresponding to unique combinations of values of the first and second plurality of response signals;

determine from the graph a first point representative of a first predetermined concentration of the component at the first ambient condition and a second point representative of a second predetermined concentration of the component at the second ambient condition, wherein a slope of a line joining the first and second points is representative of the concentration of the component; and determining the concentration of the component based on the slope.

11. The system of claim 10, wherein each of the first ambient condition and the second ambient condition comprises at least one of a temperature setting and a pressure setting.

12. The system of claim 10, wherein the light source comprises a modulated light source configured to emit a wavelength modulated laser beam to the component in the absorption cell.

13. The system of claim 12, wherein the photo detector is further configured to measure a first amplitude of a first response signal and a second amplitude of a second response signal, wherein the first response signal and the second response signal correspond to two distinct harmonics of modulating frequency of the wavelength modulated laser beam.

14. The system of claim 13, wherein the processor is further configured to normalize the first amplitude by the second amplitude.

15. The system of claim 10, wherein the photo detector is further configured to measure a direct absorbance signal.

16. The system of claim 10, wherein the processor is further configured to determine a reference response value by projecting the first and second plurality of response signals on to a reference response.

17. The system of claim 16, wherein the processor is further configured to determine a reference response value by projecting the first and second plurality of response signals on to the reference response using a non-orthogonal projection technique.

18. The system of claim 10, wherein the component comprises acetylene, hydrogen, methane, ethane, ethylene, carbon dioxide, moisture, carbon monoxide, or combinations thereof.

* * * * *